United States Patent
Al-Rashdan et al.

(10) Patent No.: US 8,814,832 B1
(45) Date of Patent: Aug. 26, 2014

(54) EXPANDABLE SHEATH AND SYSTEM FOR INTRAVASCULAR INSERTION OF A MEDICAL IMPLEMENT USING THE SAME

(71) Applicants: Ibrahim Rashid Al-Rashdan, Qortaba (KW); Eran Levit, Amherst, NH (US)

(72) Inventors: Ibrahim Rashid Al-Rashdan, Qortaba (KW); Eran Levit, Amherst, NH (US)

(73) Assignee: Ibrahim Rashid Al-Rashdan, Qortoba (KW)

( * ) Notice: Subject to any disclaimer, the term of this patent is extended or adjusted under 35 U.S.C. 154(b) by 0 days.

(21) Appl. No.: 14/056,908

(22) Filed: Oct. 17, 2013

Related U.S. Application Data

(60) Provisional application No. 61/765,213, filed on Feb. 15, 2013, provisional application No. 61/791,748, filed on Mar. 15, 2013, provisional application No. 61/792,352, filed on Mar. 15, 2013.

(51) Int. Cl.
*A61M 5/178* (2006.01)
*A61M 25/06* (2006.01)
*A61M 25/00* (2006.01)

(52) U.S. Cl.
CPC ... *A61M 25/0606* (2013.01); *A61M 2025/0024* (2013.01); *A61M 2025/0681* (2013.01)
USPC .............................. 604/164.03; 604/164.01

(58) Field of Classification Search
CPC ................. A61M 16/0488; A61M 2025/0024; A61M 2025/0063; A61M 25/01; A61M 25/0102; A61M 25/04; A61M 25/06; A61M 2025/0681
USPC .......... 604/158, 163, 164.01, 164.03, 164.09, 604/164.1, 164.11, 164.12, 164.13, 264
See application file for complete search history.

(56) References Cited

U.S. PATENT DOCUMENTS

| | | | | |
|---|---|---|---|---|
| 4,619,263 A * | 10/1986 | Frisbie et al. | .................. | 606/192 |
| 5,254,097 A * | 10/1993 | Schock et al. | ........... | 604/167.04 |
| 5,431,639 A * | 7/1995 | Shaw | ............... | 604/264 |
| 5,643,318 A * | 7/1997 | Tsukernik et al. | ............ | 606/214 |
| 6,183,443 B1 * | 2/2001 | Kratoska et al. | .......... | 604/164.03 |
| 6,652,492 B1 | 11/2003 | Bell et al. | | |
| 8,226,619 B2 | 7/2012 | Miller et al. | | |
| 8,282,664 B2 * | 10/2012 | Nance et al. | ................... | 606/191 |
| 2004/0006344 A1 * | 1/2004 | Nguyen et al. | ................... | 606/72 |
| 2006/0058739 A1 * | 3/2006 | Smith et al. | .................... | 604/246 |
| 2008/0082083 A1 | 4/2008 | Forde et al. | | |
| 2009/0192452 A1 * | 7/2009 | Sasajima et al. | ........... | 604/99.04 |
| 2009/0312710 A1 * | 12/2009 | Smith | ...................... | 604/164.03 |
| 2010/0204684 A1 | 8/2010 | Garrison et al. | | |
| 2010/0324490 A1 * | 12/2010 | Pini et al. | ................. | 604/167.03 |
| 2010/0331612 A1 | 12/2010 | Lashinski et al. | | |
| 2011/0112567 A1 * | 5/2011 | Lenker et al. | ................ | 606/194 |
| 2011/0245775 A1 * | 10/2011 | Tekulve | ........................ | 604/171 |
| 2012/0053614 A1 * | 3/2012 | Mukherjee | ................... | 606/194 |
| 2012/0158033 A1 | 6/2012 | Deal et al. | | |
| 2013/0184735 A1 | 7/2013 | Fischell et al. | | |

* cited by examiner

*Primary Examiner* — Quynh-Nhu H Vu
(74) *Attorney, Agent, or Firm* — Richard C. Litman

(57) ABSTRACT

The expandable sheath and system for intravascular insertion of a medical implement includes a cannula for entering a lumen of a vascular vessel of a patient, a guide wire insertable into the lumen, an introducer and dilator adapted to follow the guide wire into the lumen, an expandable sheath positioned on the introducer and dilator, with the expandable sheath being adapted to be positioned in the vessel, and an extension collar. The medical implement is received within the vessel by passing through the sheath upon separating the introducer and dilator therefrom. In one embodiment, a linear array of perforations formed through the expandable sheath allow for expansion. Alternatively, an external slit may be provided for selective expansion of the sheath.

8 Claims, 8 Drawing Sheets

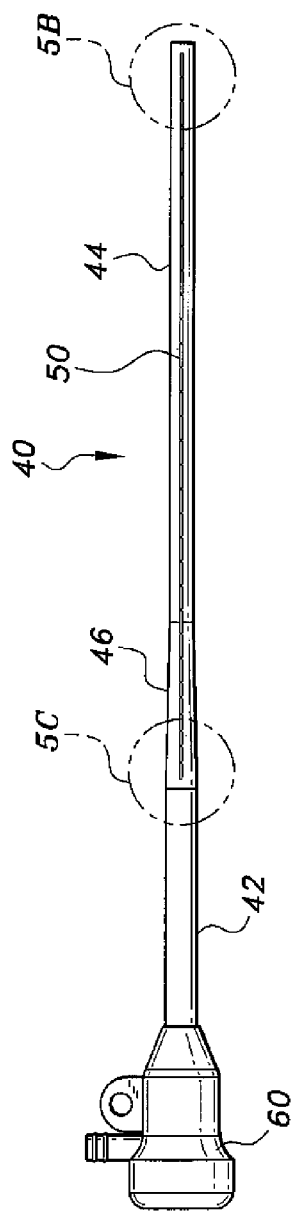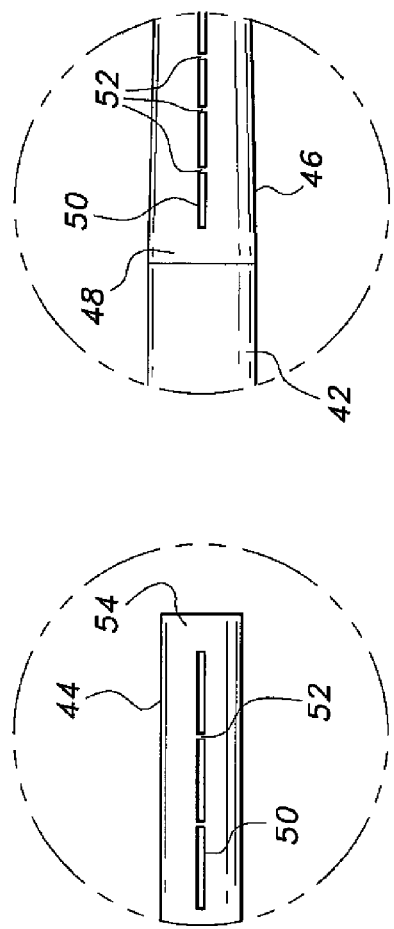

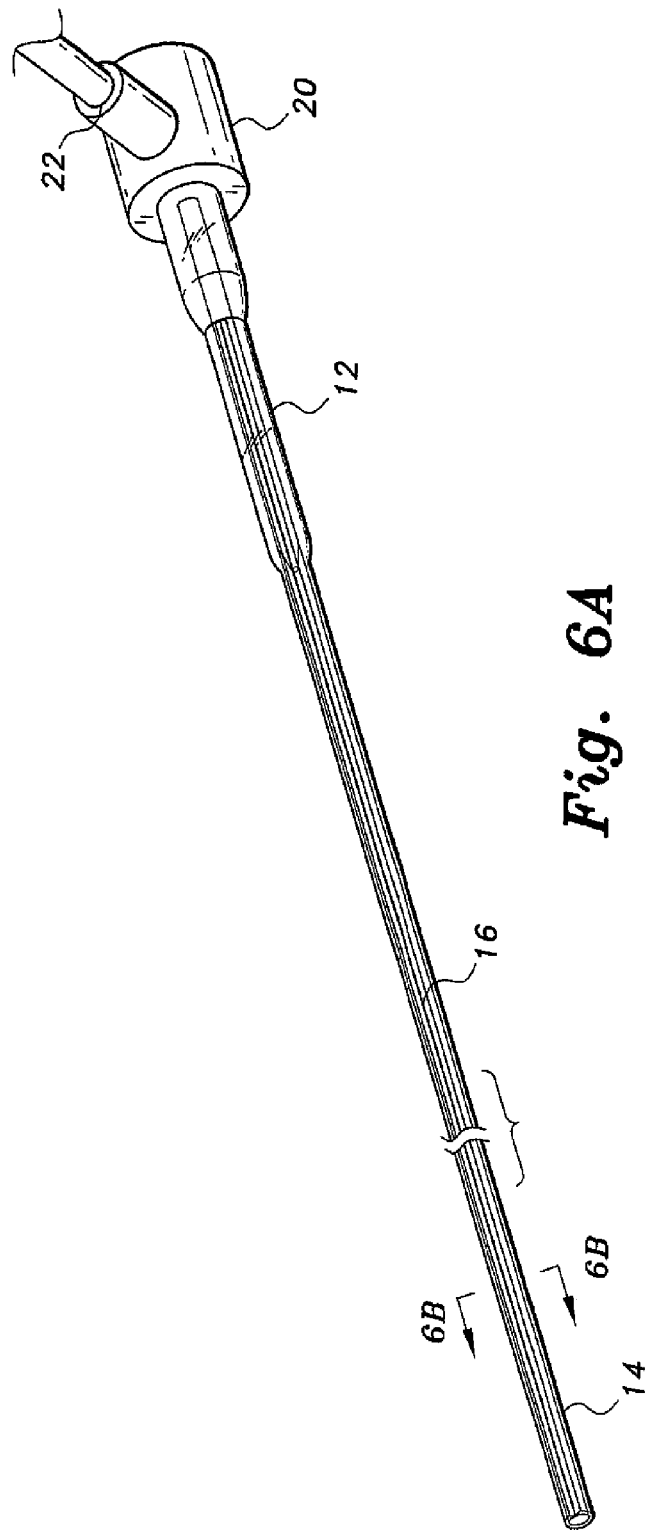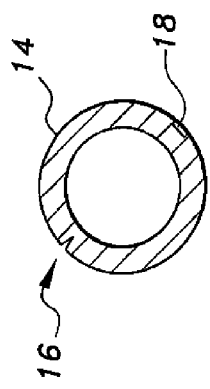

EXPANDABLE SHEATH AND SYSTEM FOR INTRAVASCULAR INSERTION OF A MEDICAL IMPLEMENT USING THE SAME

CROSS-REFERENCE TO RELATED APPLICATIONS

This application claims the benefit of U.S. Provisional Patent Application Ser. No. 61/765,213, filed Feb. 15, 2013; U.S. Provisional Patent Application Ser. No. 61/791,748, filed Mar. 15, 2013; and U.S. Provisional Patent Application Ser. No. 61/792,352, filed Mar. 15, 2013.

BACKGROUND OF THE INVENTION

1. Field of the Invention

The present invention relates to medical devices, and particularly to an expandable sheath for insertion of an arterial catheter.

2. Description of the Related Art

Less invasive medical procedures for various operations are, of course, highly desirable, as they result in less trauma for the patient, faster healing, less time spent in the hospital, less expense to the patient, and the ability for the patient to return to his or her work or normal lifestyle more rapidly. This is particularly true in cardiac procedures. If a surgical procedure can be accomplished without an open chest, or open-heart, surgery, such less invasive practices are much more desirable.

An example of such is the opening of various coronary arteries that have become obstructed by cholesterol deposits. The correction of this condition originally required surgery to access the interiors of the arteries directly for curettage. More recently, such arterial deposits have been flattened or pressed against, or into, the walls of the arteries by the balloon angioplasty procedure, wherein an inflatable device is inserted into the artery and expanded to widen the artery for proper blood flow. Accessing the femoral artery in one of the thighs of the patient, and working a catheter through the artery until reaching the desired target area in the coronary artery conventionally accomplish this procedure. The balloon is expanded to widen the artery when the balloon reaches the target area. While this procedure is clearly less invasive than open chest surgery, the length of the catheter and sheath required, as well as the delicate manipulation of the catheter and sheath through such a relatively long pathway, make this a relatively intricate procedure. Various other procedures, such as coronary angioplasty, coronary arteriography, cardiac catheterization, etc., also typically involve the insertion of catheters, guides, and the like through an introducer sheath in the femoral artery.

More recently, there has been interest in developing techniques for access of coronary arteries through the radial artery in the wrist or lower arm of the patient. This procedure has advantages, including the far shorter distance required for manipulation of the distal end of the catheter from the entry site to the coronary artery. This also generally results in fewer traumas to the patient, as the percutaneous opening need not be so large when accessing the smaller radial artery in comparison to the femoral artery. However, the radial artery is a smaller diameter vessel than the femoral artery. Generally, it is desirable to keep the puncture of the vessel as small as possible. Nevertheless, coronary procedures often require the use of larger diameter guides, catheters, etc., than desirable in the radial artery.

The medical profession uses a measurement system known as the French system for the diameters of these various sheaths and catheters. In the French system, one French is equal to one third of a millimeter, i.e., 3 F=1.0 mm, with a linear correspondence between the French and metric dimensions. Typical guide and sheath diameters for use in a radial artery intervention procedure might be 2.00 mm or 6 French for the sheath, but the use of a larger 2.33 mm or 7 French guide is desirable in order to provide sufficient volume within the guide for the catheters and guides used for coronary procedures.

Thus, an expandable sheath and system for intravascular insertion of a medical implement using the same solving the aforementioned problems is desired.

SUMMARY OF THE INVENTION

The expandable sheath and system for intravascular insertion of a medical implement includes a cannula for entering a lumen of a vascular vessel of a patient, a guide wire insertable into the lumen, an introducer and dilator adapted to follow the guide wire into the lumen, an expandable sheath positioned on the introducer and dilator, with the expandable sheath being adapted to be positioned in the vessel, and an extension collar. The medical implement is received within the vessel by passing through the sheath upon separating the introducer and dilator therefrom.

The expandable sheath is formed as an elongate flexible tubular member adapted for placement percutaneously within the vessel of the patient. The tubular member is preferably formed of a polymer material and includes a wall of substantially uniform thickness. The wall has an outer surface and an inner surface, with the wall having a first portion, a transitional portion and a second portion respectively having first, transitional and second inner diameters associated therewith. The first inner diameter is greater than the second inner diameter, and the transitional inner diameter is less than the first inner diameter and greater than the second inner diameter, such that, upon placement in the vessel, the sheath is adapted to slidably receive intravascular devices therein. In one embodiment, the tubular member includes a linear array of perforations formed therethrough, with the linear array of perforations extending from the second portion to the transitional portion, such that the linear array of perforations allow the second and transitional portions to expand.

These and other features of the present invention will become readily apparent upon further review of the following specification and drawings.

BRIEF DESCRIPTION OF THE DRAWINGS

FIG. 5A is an elevational view of an alternative embodiment of the expandable sheath and system for intravascular insertion of a medical implement using the same.

FIG. 5B is an enlarged view of the portion 5B of the expandable sheath and system for intravascular insertion of a medical implement using the same of FIG. 5A.

FIG. 5C is an enlarged view of the portion 5C of the expandable sheath and system for intravascular insertion of a medical implement using the same of FIG. 5A.

FIG. 6A is an elevational view of another alternative embodiment of the expandable sheath and system for intravascular insertion of a medical implement using the same.

FIG. 6B is cross-sectional view taken alone sectional cut line 6B-6B of FIG. 6A.

Similar reference characters denote corresponding features consistently throughout the attached drawings.

DETAILED DESCRIPTION OF THE PREFERRED EMBODIMENTS

Figure 1:
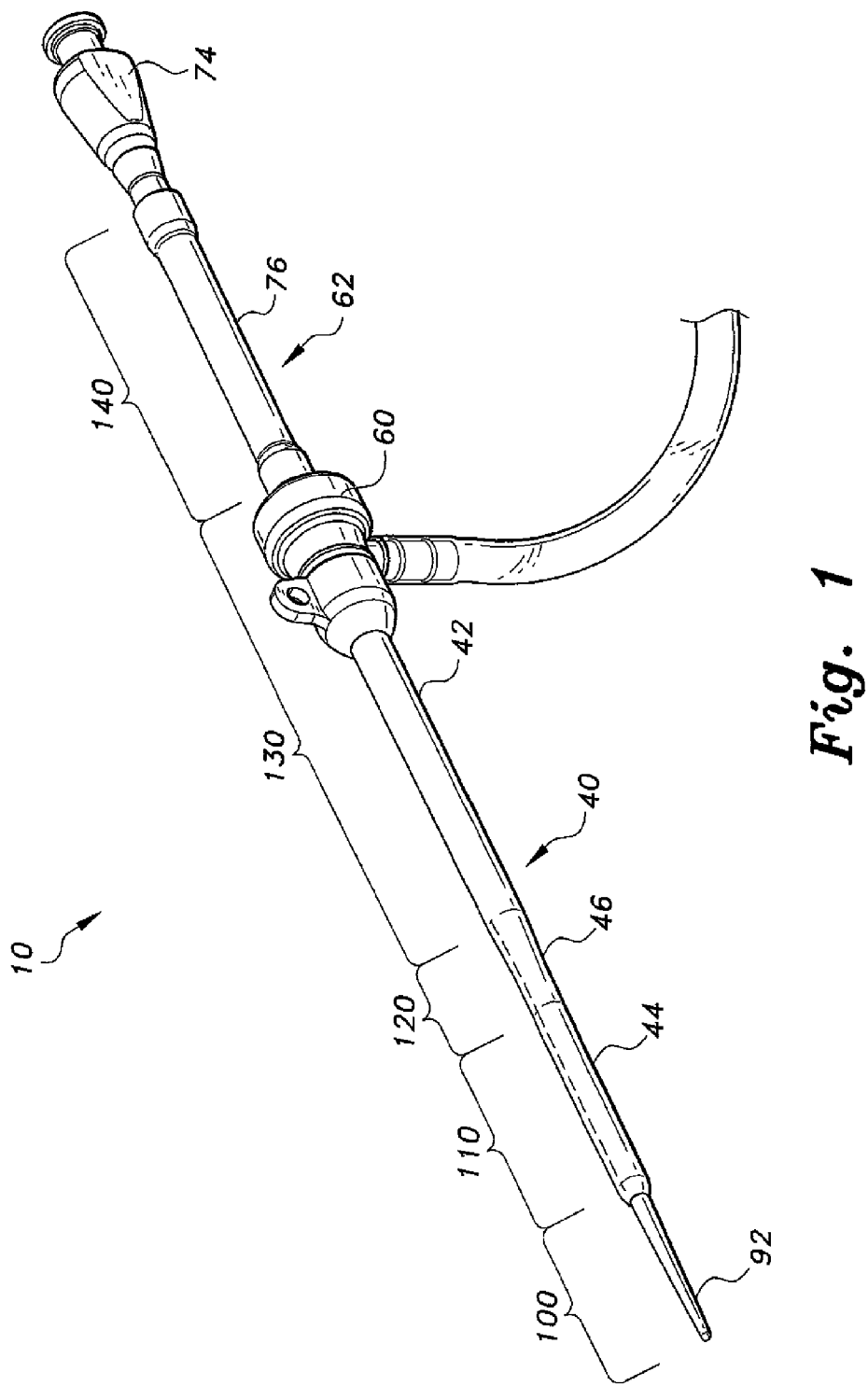
FIG. 1 is a perspective view of an expandable sheath and system for intravascular insertion of a medical implement using the same according to the present invention.

The expandable sheath and system for intravascular insertion of a medical implement, as shown in FIG. 1, generally identified as 10, includes an introducer and dilator 62 having a proximal end 74, a collar 76, a sheath 40, and a hub 60. The sheath 40 has a proximal end 42, a transitional area 46, and a distal end 44. The sheath is shown disposed about the introducer and dilator 62, with the distal end 92 of introducer and dilator 62 shown extending from the distal end 44 of sheath 40. The hub 60 may include, or be connected with, vascular procedural specific components, such as a hemostasis valve, for example.

Figure 2:
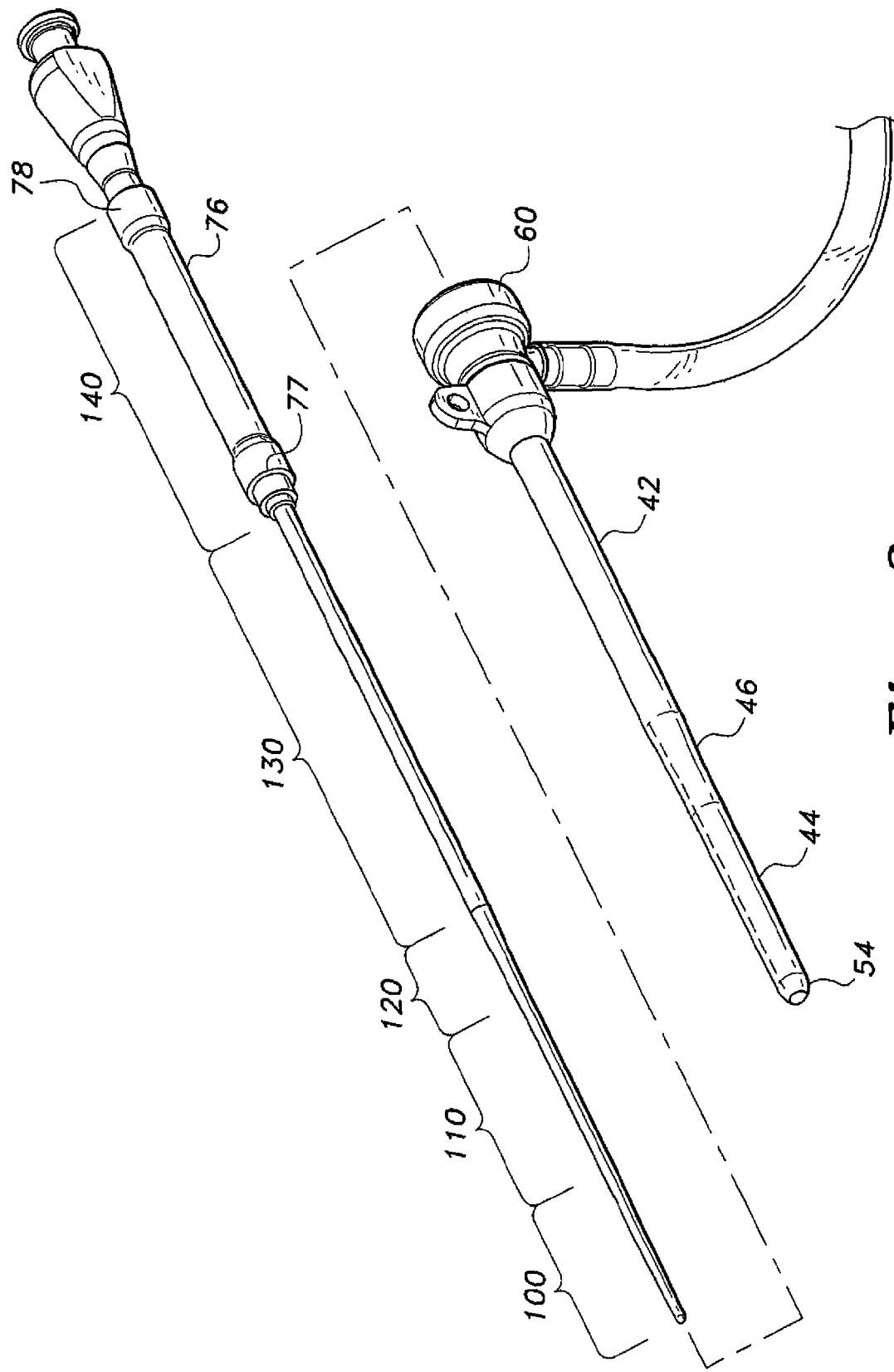
FIG. 2 is a partially exploded perspective view of an expandable sheath and system for intravascular insertion of a medical implement using the same according to the present invention.
Figure 3:
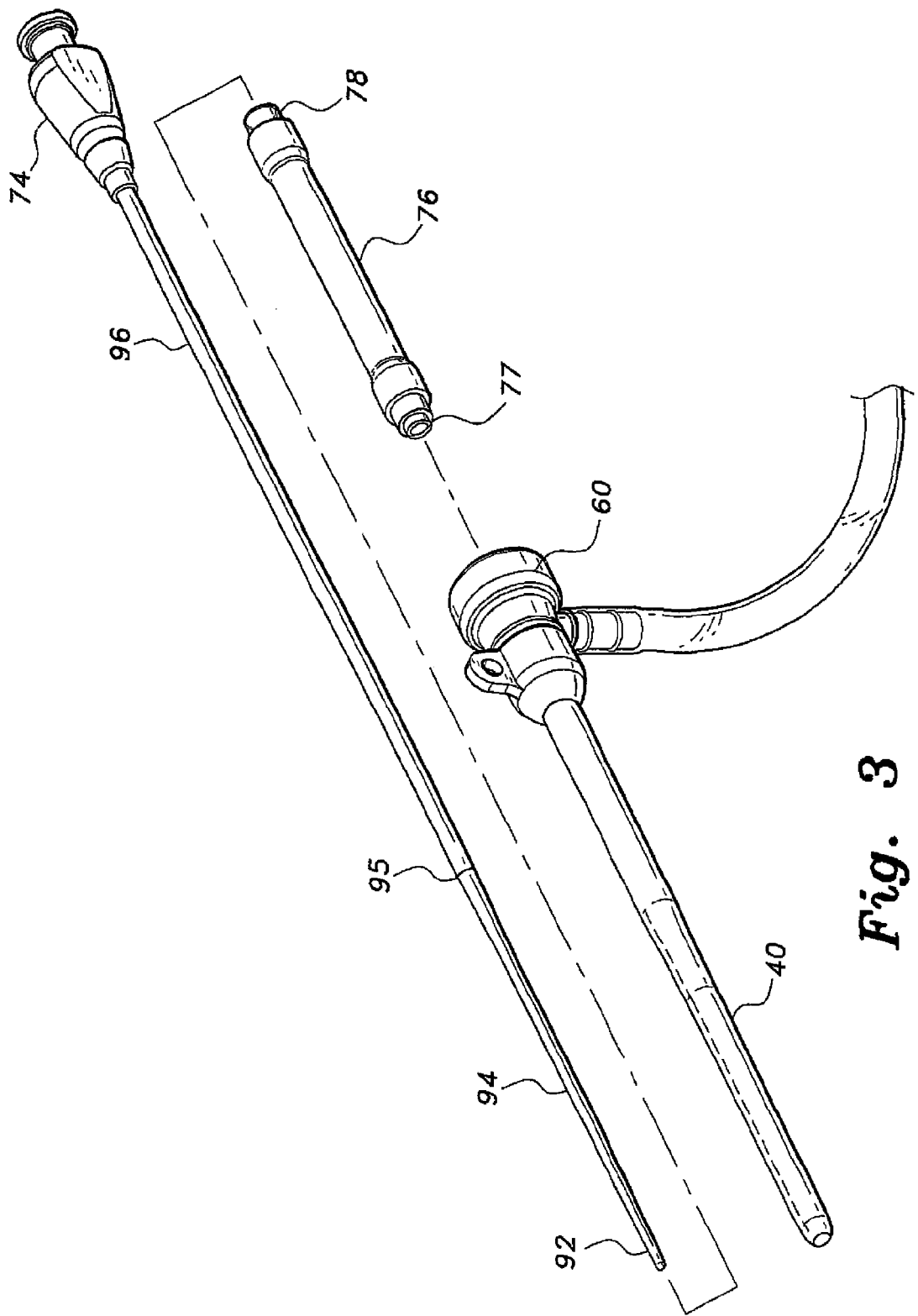
FIG. 3 is a further partially exploded perspective view of an expandable sheath and system for intravascular insertion of a medical implement using the same according to the present invention.

As shown in FIGS. 1-3, the overall length of the system 10 is segmented into five general regions. Each region has a specific geometrical form, and function, discussed below. Section 100 represents the distal end 92 of introducer and dilator 62, section 110 includes the portion 94 of the introducer and dilator 62 (as shown in FIG. 3), upon which the distal end 44 of sheath 40 is mounted. Section 120 represents the transitional portion 95 of introducer and dilator 62, and the corresponding transitional section of 46 of sheath 40. Section 130 includes a part of portion 96 of introducer and dilator 62, and the proximal end 42 of the sheath, and hub 60 (connected to the proximal end 42). Section 140, includes the remaining portion 96 of the introducer and dilator 62, along with an extension collar 76.

Figure 7:
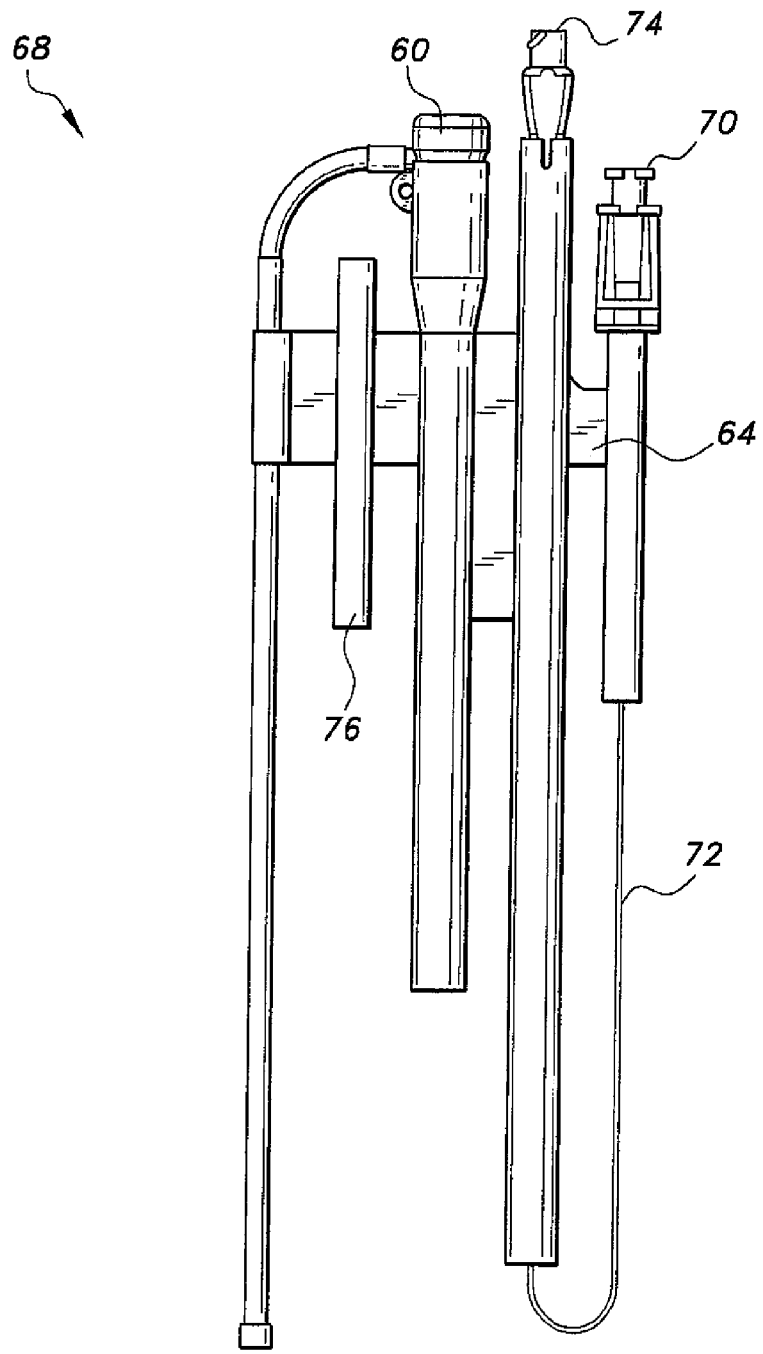
FIG. 7 illustrates a kit including the expandable sheath and system for intravascular insertion of a medical implement using the same.
Figure 8:
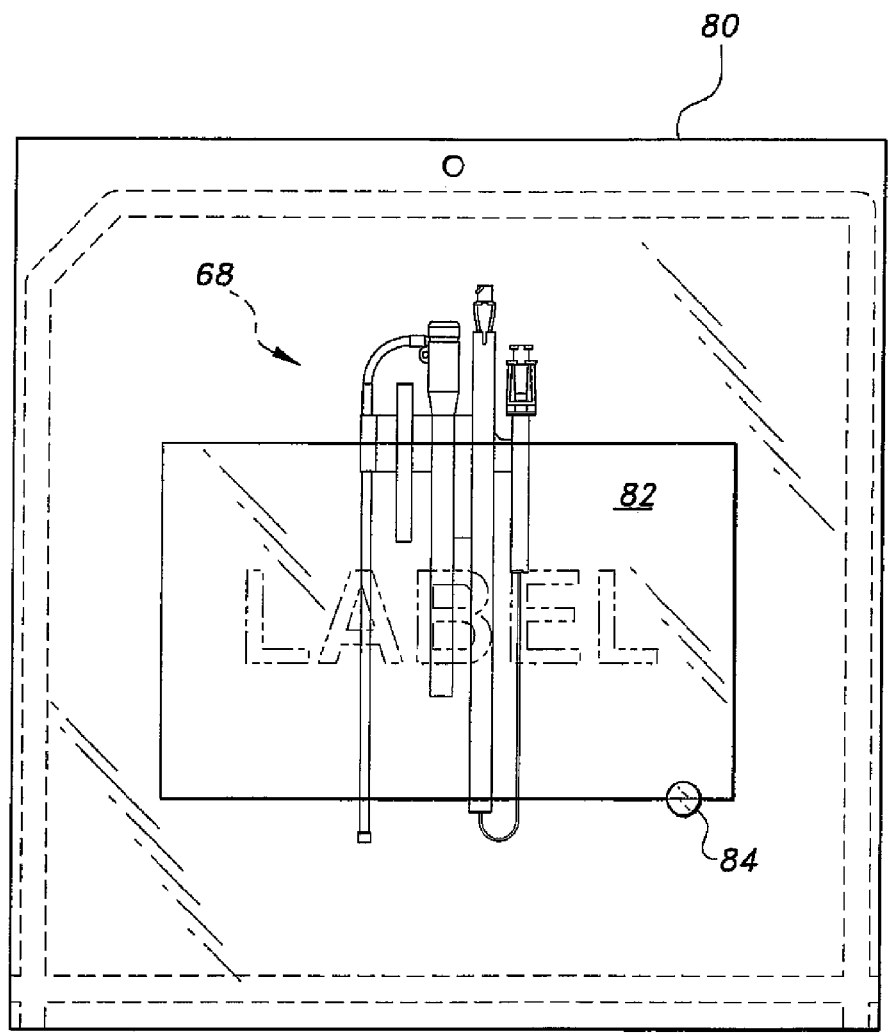
FIG. 8 illustrates the kit of FIG. 7 provided in sterile packaging.

As shown in FIGS. 7 and 8, a cannula 70 and guide wire 72 are provided for introduction into the lumen of a vascular member. Initially, the cannula 70 is used to puncture the skin, tissue, and vascular vessel, penetrating into the lumen. The guide wire 72 is subsequently introduced via the cannula 70 into the vessel, and remains traversing the skin, tissue, and vessel wall upon removal of the cannula 70. The system 10 is thusly placed about the guide wire 72 (via the hollow interior of the introducer and dilator 62), and extended into the vessel lumen. The distal end 92 of the introducer and dilator 62 is tapered so as to gradually enter the aperture produced by the cannula 70, increasing the aperture as the introducer and dilator 62 proceeds into the lumen. As best shown in FIG. 2, the distal end of the sheath 44 includes a tapered or rounded tip 54 that follows the distal end 92 of the introducer and dilator 62, gradually increasing the size of the aperture leading into the vessel without causing any undue harm or injury to the skin, tissue, and vessel.

The proximal end 42 of the sheath 40 may be color coded, or have indicia markings to indicate orientation and depth of penetration into the vessel. Once the desired penetration depth has been achieved, the introducer and dilator 62 is removed, and another implement, such as a catheter, for example, may be inserted into the vessel via the sheath 40. The characteristics of the sheath 40 allow the catheter to enter into the vessel without causing any undue harm or injury to the vessel. The sheath 40 has, at its proximal end 42, a first inner diameter, and at its distal end 42 a second inner diameter.

Generally, the first inner diameter is larger than the second inner diameter. For example, the first inner diameter may be 8 Fr., while the second inner diameter may be 6 Fr. Between the proximal end 42 and the distal end 44 is a gradual transitional section 46 that connects the first inner diameter to the second inner diameter through a smooth, decrease in radial direction. This allows, for example, a gradual sloping from the 8 Fr. to the 6 Fr. inner diameters of the sheath 40. The hub 60, also has an inner diameter of 8 Fr. in alignment with the inner diameter of the proximal end 42 of sheath 40. In operation, a medical practitioner is able to safely insert a medical implement, such as a balloon catheter of 6 Fr. diameter into the vessel via the sheath 40.

The introducer and dilator 62 has corresponding outer diameters with the inner diameters of the sheath 40, in accordance with the sections 100-140 discussed above. Beginning from the tapered distal end 92 of introducer and dilator 62, segment 110, or portion 94, has an outer diameter equal to the inner diameter of distal end 44 of sheath 40, for example, 6 Fr. The outer diameter of the transition segment 120, or portion 95, of introducer and dilator 62 matches the inner diameter of transition section 46 of sheath 40. Likewise, the outer diameter of segment 130, or portion 96, of introducer and dilator 62 is equal to the inner diameter of proximal end 42 of sheath 40.

Situated about the extension of portion 96 is collar 76. Collar 76 has a first end 77 that matingly engages the hub 60 of sheath 40. As shown in FIG. 3, collar 76 has a second end 78 that forms a stop for the end piece 74 of introducer and dilator 62. The collar 76 prevents the introducer and dilator 62 from being inserted further into the sheath 40 than the depth of penetration indicia of the sheath requires. More importantly, this is the case when medical implements, such as catheters having maximum diameters of 6 Fr., are being used for vascular procedures. Collar 76 preferably releasably locks with both end piece 74 of introducer and dilator 62 and with sheath hub 60. It should be understood that any suitable type of locking mechanism or releasable connector may be utilized. As an alternative, collar 76 may be replaced by a peel-away or tear-away collar, thus saving time in the conventional procedure, in which the dilator is removed, the collar is then removed, and then the dilator is re-inserted.

If the need arises for medical implements having a greater diameter, such as 7 Fr. or 8 Fr., for example, conventional prior art systems require a different sheath to be inserted, which requires the removal of the first sheath, possibly causing blood loss and other injury to the vessel and surrounding tissue. The sheath 40, however, avoids delay in catheter insertion due to repenetration of the introducer and dilator 62 and sheath 40. Sheath 40 includes structure that allows for the expansion of the second inner diameter, as well as the transitional diameter, so that the inner diameter of the sheath 40 is uniformly the same as the first inner diameter of the proximal end 42.

In the alternative embodiment of FIGS. 5A-5C, sheath 40 has a linear array of perforations 50 formed therethrough. The perforations 50 extend from transition section 46 to near the tip of distal end 44. As best shown in the enlarged views of FIGS. 5B and 5C, the perforations 50 are preferably linear, with each perforation 50 being separated from the adjacent perforation by a segment 52. The perforations 50 begin at the tip 54 without breaching the open end of distal end 44 (see FIG. 5B). Likewise, the perforations 50 end near the junction of the proximal end 42 and transition portion 46, such that that a space 48 prevents the perforations from encroaching into the proximal end 44. It should be understood that the linear perforations are shown for exemplary purposes only, and that the perforations may have any desired contouring and relative dimensions, such as circular, elliptical, etc. Additionally, as best shown in the comparison between FIGS. 5B and 5C, the perforations 50 toward the distal end of the sheath 40 are preferably longer to allow for less resistance while introducing the larger portion of the dilator and to expand the sheath with less force.

In the embodiment of FIGS. 6A and 6B (taken along direction 6B-6B of FIG. 6A), the sheath 40 may be an elongated cylindrical tube having a large diameter portion 12 at the proximal end thereof (for example, with an inner diameter of 8 Fr.) with an elongated slit 16 extending longitudinally from the distal end of the sheath towards the large diameter portion. It will be understood that the slit 16 may extend for more than one-half the length of the sheath 40, and may extend up to 80-90% of the length of the sheath 40, extending from the smaller diameter portion 14 of sheath 40 (having a diameter of 6 Fr., for example). The slit, by using a circular blade with gr 16 may be formed by any suitable method, such as, for example ooves. When such a blade is rolled on the sheath, the grooves leave non-slit portions between the slits created by the circular blade. The slit portion 16 is preferably formed so that the edges of the slit are harmless to the arterial wall. In the formation example given above, the way the blade edges are formed, the sharp edges of the blade slit the tube and the slit edges are compressed by the non-sharpened edges and form non-traumatic edges on both sides of slit.

The slit 16 in portion 14 is kept tight to prevent bleeding. The slit 16 must avoid bleeding when sheath 40 is introduced into the artery and is used within its original dimensions (i.e., non-expanded) to deliver catheterization tools with the outside diameter smaller than the inner original diameter (i.e., non-expanded) of the sheath. Additionally, as shown in FIG. 6B, indicia 18 may also be formed on the sheath 40 to indicate orientation, penetration depth, and any other desired positional characteristic of the sheath 40. Indicia 18 may include markings, etchings, arrows, and/or color-coding along the entire length of sheath 40. Indicia 18 preferably is formed on the proximal end 42, so as to extend outside the radial artery (upon insertion), away from the patient. As an alternative to the pre-formed perforations 50 of FIGS. 5A-5C or the pre-formed external slit 16 of FIGS. 6A and 6B, the dilator could be provided with a blade or the like for creating a continuous internal slit as the sheath 40 is inserted thereon. Such a blade or the like mounted on dilator 78, preferably between sections 110 and 120, would create an internal slit, allowing for expansion as described above with regard to both perforations 50 and external slit 16.

The purpose of the perforations 50 (FIGS. 5A-C) and slit 16 (FIGS. 6A and 6B) is to provide the medical practitioner with the ability to utilize a single system for multiple sized catheters during an intravascular procedure. The sheath 40 in both embodiments is expandable, thus increasing the second inner diameter and the transitional diameter to match the first inner diameter; i.e., expanding the transition section 46 and distal end 44 so that the respective inner diameters match the larger inner diameter of the proximal end 42. In the example described above, the 6 Fr. distal diameter is expanded to match the 8 Fr. proximal diameter.

Figure 4:
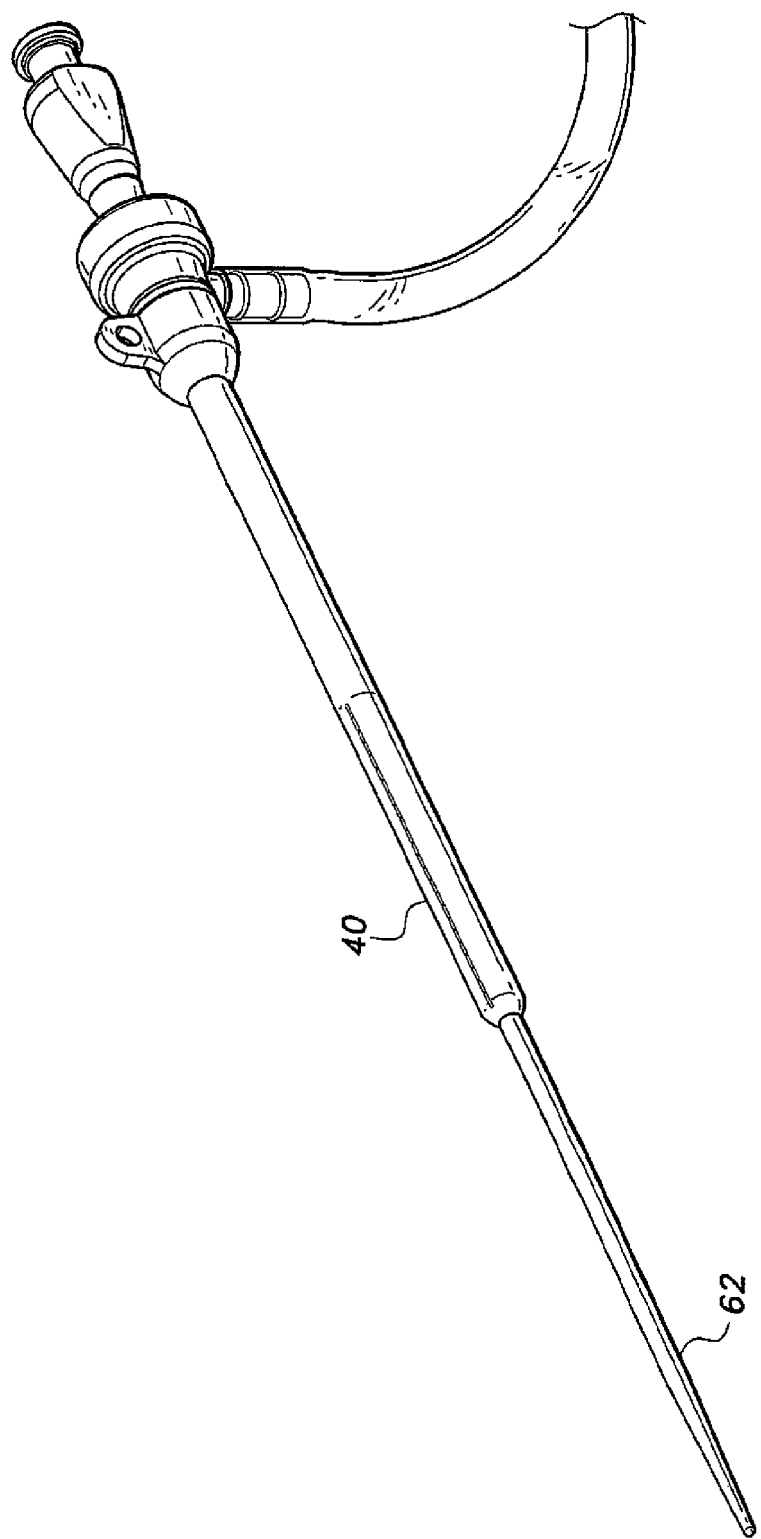
FIG. 4 is a perspective view of the expandable sheath and system for intravascular insertion of a medical implement using the same.

As best shown in FIGS. 3 and 4, after the system 10 has been inserted into a vessel, the introducer and dilator 62 is withdrawn from sheath 40, the extension collar 76 is removed by disengaging the first end 77 from the hub 60. The introducer and dilator 62 is reinserted into the sheath 40 via hub 60, and is extended along the length of the segment 140 (i.e., the remaining part of portion 96). Upon reinsertion, the transitional portion 95 of introducer and dilator 62 forces the transitional section 46 and distal end 44 of sheath 40 radially outward so that the inner diameter is consistent throughout the sheath 40. The proximal end portion 96 of the introducer and dilator 62 has an outer diameter equal to the inner diameter of proximal end of the sheath 40, thus maintaining the expansion until the introducer and dilator 62 has traveled the full extent of the length through the five segments 100, 110, 120, 130, 140.

As shown in FIG. 4, the sheath 40 has a constant diameter externally, indicative of the internal diameter also being constant. In this particular example, the inner diameter has been expanded to 8 Fr., thereby allowing the medical practitioner to utilize implements that are greater than 6 Fr. in the sheath 40. Once the introducer and dilator 62 is removed, the expanded sheath allows the larger diameter implements to be inserted into the vascular vessel. Further, it is clear that the introducer and dilator 62 is a single element used in the system for both guiding the sheath 40 into the vessel, as well as causing the sheath 40 to be expanded.

Additionally, the first end 77 of collar 76 is designed and configured to matingly engage the hub 60 of sheath 40. The mating engagement may be accomplished in any suitable manner, including, but not limited to, friction fit, threads, twist lock, key and channel, dovetail, etc. Likewise, the second end 78 of the collar 76, which stops the forward progression of the introducer and dilator 62 into the sheath 40, may also be a mating engagement, similar to the first end and 77 with hub 60, forming an abutment for the end 74 to stop against.

In the embodiment of FIGS. 5A-C, sheath 40 may be made from any suitable polymer or plastic material that has sufficient plasticity so that, upon the expansion of the perforations 50, the sections 52 will stretch to accommodate the larger diameter, but upon removal of the introducer and dilator 62, sections 52 will not return to the original shape. Similarly, the sheath 40 in FIGS. 6A and 6B, upon insertion of the introducer and dilator 62, causing the seam to split along the slit 16 and expand to accommodate larger implements inserted through the sheath 40, the sheath 40 will retain its shape with the slit 16 opened. The sheath 40 may made from a single, homogenous layer of material. It should be understood that the contouring and relative dimensions of both slit 16 and perforations 50 may be varied, and those shown have been shown for exemplary purposes and for purposes of clarity only.

Referring to FIGS. 7 and 8, the sheath 40 is part of a complete system 68 for introducing medical implements into the vascular system of a patient. The complete system 68 includes, as shown in FIG. 7, a holder, such as holster 64, an introductory cannula 70, a guide wire 72, the expandable sheath 40, and a stepped dilator 74. The holster 64 includes a mount 76 for supporting the complete system 68 in proximity to the patient during installation into a blood vessel. The complete system 68 may be provided in packaging 80, as shown in FIG. 8, so as to be completely sterile when needed. The packaging 80 has an indicator 84 for identifying that the contents, namely the complete system 68 and its components, are sterile. The package also has a label 82 with indicia for identifying the contents, as well as instructions on usage, warnings, and dates of manufacture, use by, and/or expiration.

It is to be understood that the present invention is not limited to the embodiments described above, but encompasses any and all embodiments within the scope of the following claims.

We claim:

1. A system for intravascular insertion of a medical implement, comprising:
    a cannula for entering a lumen of a vascular vessel of a patient;
    a guide wire insertable into the lumen;
    wherein after insertion of guide wire, the cannula is removed from the vascular vessel of the patient;
    an introducer and dilator adapted to follow the guide wire into the lumen;
    an expandable sheath positioned on the introducer and dilator, the sheath defining an elongate flexible tubular member including a proximal end and an open distal end, the expandable sheath being adapted to be positioned in the vessel, the expandable sheath including:
        i) a wall of substantially uniform thickness, the wall having an outer surface and an inner surface, the wall having a first portion, a transitional portion and a second portion respectively from the proximal end to the distal end and having first, transitional and second inner diameters associated therewith,
        ii) the first inner diameter being greater than the second inner diameter, the transitional inner diameter being less than the first inner diameter and being greater than the second inner diameter,
        iii) the first portion only of the expandable sheath further including indicia for proper orientation and positioning of the expandable sheath upon entry into the vascular vessel of the patient,
        iv) an array of perforations formed therethrough, the array of perforations extending only from the second portion to the transitional portion, whereby the array of perforations allow the second and transitional portions to expand, wherein the length of the perforations on the second portion are longer than the length of perforations on the transitional portion thereby the second end provides less resistance to expansion,
        v) the perforations of the second portion terminate adjacent the open end of the distal end of the sheath thereby not breaching the open end; and
    an extension collar, wherein the medical implement may be received within the vessel by passing through the sheath upon separating the introducer and dilator therefrom.

2. The system for intravascular insertion of a medical implement as recited in claim 1, further comprising a hub attached to the proximal end of the sheath, the indicia indicating the alignment of the hub with the sheath.

3. The system for intravascular insertion of a medical implement as recited in claim 1, wherein the array of perforations includes a linear array of perforations.

4. The system for intravascular insertion of a medical implement as recited in claim 1, whereby the introducer and dilator pass through the first portion of the wall of the sheath, and upon entering the transitional portion, and subsequently the second portion of the sheath, cause the sheath to expand radially as the introducer and dilator force the perforations to expand along the linear array.

5. The system for intravascular insertion of a medical implement as recited in claim 4, wherein the extension collar includes a releasable connector for releasably engaging the hub of the sheath opposite the first portion, a tubular member extending from the releasable connector, and an end stop opposite the releasable connector.

6. The system for intravascular insertion of a medical implement as recited in claim 5, wherein the extension collar further comprises a secondary releasable connector for releasably engaging a hub of the introducer and dilator.

7. An expandable sheath for introducing intravascular devices percutaneously within a vessel of a patient, comprising:
    an expandable sheath, the sheath defining an elongate flexible tubular member including:
        i) a proximal end and an open distal end, the expandable sheath being adapted to be positioned in the vessel; the expandable sheath including a wall of substantially uniform thickness, the wall having an outer surface and an inner surface, the wall having a first portion, a transitional portion and a second portion respectively from the proximal end to the distal end and having first, transitional and second inner diameters associated therewith, the first inner diameter being greater than the second inner diameter, the transitional inner diameter being less than the first inner diameter and being greater than the second inner diameter,
        ii) the first portion only of the expandable sheath further including indicia for proper orientation and positioning of the expandable sheath upon entry into the vascular vessel of the patient,
        iii) an array of perforations formed therethrough, the array of perforations extending only from the second portion to the transitional portion, whereby the array of perforations allow the second and transitional portions to expand, wherein the length of the perforations on the second portion are longer than the length of perforations on the transitional portion thereby the second end provides less resistance to expansion,
        iv) the perforations of the second portion terminate adjacent the open end of the distal end of the sheath thereby not breaching the open end.

8. The expandable sheath for introducing intravascular devices as recited in claim 7, wherein the array of perforations on the sheath defines a linear array of perforations.

* * * * *